United States Patent

Aloup et al.

Patent Number: 5,120,852
Date of Patent: Jun. 9, 1992

[54] PROCESS FOR PREPARING (1R,2R)-2-(3-PYRIDYL)-TETRAHYDROTHIOPYRAN-2-CARBOTHIOAMIDE 1-OXIDES THEREBY

[75] Inventors: Jean-Claude Aloup, Villeneuve Le Roi; Claude James, Paris; Rodolphe Margraff, Viry Chatillon, all of France

[73] Assignee: Rhone-Poulenc Sante, Antony, France

[21] Appl. No.: 607,003

[22] Filed: Oct. 31, 1990

[30] Foreign Application Priority Data

Oct. 31, 1989 [FR] France .................. 89 14273

[51] Int. Cl.$^5$ ........................... C07D 409/04
[52] U.S. Cl. ................................. 546/268
[58] Field of Search ...................... 546/268

[56] References Cited

U.S. PATENT DOCUMENTS 3,395,142 7/1968 Clemens .................. 564/74

FOREIGN PATENT DOCUMENTS 46417 2/1982 European Pat. Off. .
97584 1/1984 European Pat. Off. .
2046265 11/1980 United Kingdom .

OTHER PUBLICATIONS

Morrison et al. Organic Chemistry p. 367, pp. 371–383.

Primary Examiner—Jane T. Fan
Attorney, Agent, or Firm—Morgan & Finnegan

[57] ABSTRACT

Process for preparing (1R,2R)-2-(3-pyridyl)tetrahydrothiopyran-2-carbothioamide 1-oxides of general formula:

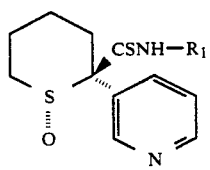

($R_1$ = alkyl containing 1 to 4 carbon atoms), by the action of an alkyl isothiocyanate on the 1R,2R and 1R,2S sulphoxides of formulae:

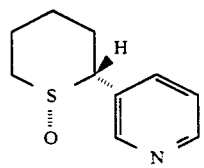

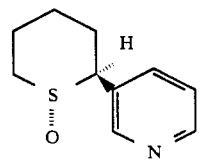

employed alone or mixed, the (1R,2R)-2-(3-pyridyl)tetrahydrothiopyran-2-carbothioamide 1-oxides thereby obtained and pharmaceutical compositions containing them.

(1R,2R)-2-(3-Pyridyl)tetrahydrothiopyran-2-carbothioamide 1-oxides are especially useful as antihypertensives.

3 Claims, No Drawings

PROCESS FOR PREPARING (1R,2R)-2-(3-PYRIDYL)-TETRAHYDROTHIOPYRAN-2-CARBOTHIOAMIDE 1-OXIDES THEREBY

FIELD OF THE INVENTION

The present invention relates to a process for preparing (1R,2R)-2-(3-pyridyl)tetrahydrothiopyran-2-carbothioamide 1-oxides, which possess especially advantageous antihypertensive properties.

BACKGROUND OF THE INVENTION

Thioformamide derivatives of general formula:

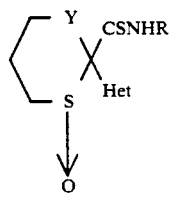

(I)

in which R represents a hydrogen atom or an alkyl radical containing 1 to 4 carbon atoms, Het represents a heterocyclic radical aromatic in nature and Y represents a valency bond or a methylene radical, have been described in European Patent EP 0,097,584.

The presence of two centers of asymmetry leads to 4 stereoisomers which can be optionally separated into 2 racemic pairs which were designated "Form A" (or more polar product) and "Form B" (or less polar product) [the polarity being determined by thin-layer chromatography (TLC)]. These two forms may be resolved.

Among the products of general formula (I), the A form of N-methyl-2-(3-pyridyl)tetrahydrothiopyran-2-carbothioamide 1-oxide consists of a mixture of the transisomers which may be represented in the following manner:

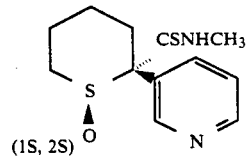

(II)

and

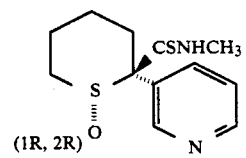

(III)

Studies performed on the isomers (II) and (III) have enabled it to be shown that the active form is the isomer (III), the absolute configuration of which is 1R,2R.

DETAILED DESCRIPTION OF THE INVENTION

The present invention relates to a process for preparing the 1R,2R derivatives of the thioformamide of general formula:

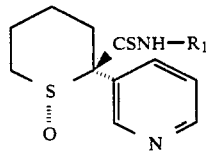

(IV)

in which $R_1$ represents a linear or branched alkyl radical containing 1 to 4 carbon atoms.

According to the invention, the products of general formula (IV) may be obtained by the action of an alkyl isothiocyanate of general formula:

$$S=C=N-R_1 \qquad (V)$$

in which $R_1$ is defined as above, on a previously anionized sulphoxide of formula:

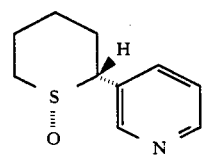

(VI)

or

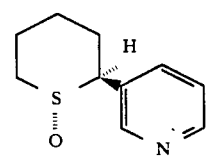

(VII)

In general, the reaction is performed by adding a solution of a sulphoxide of formula (VI) or (VII) or of a mixture of the sulphoxides of formulae (VI) and (VII) in an inert organic solvent such as an ether, e.g. tetrahydrofuran, to sodium amide (optionally prepared in situ) in liquid ammonia, working at the boiling point of the reaction mixture, i.e. at −30° C., and then adding a solution of an isothiocyanate of general formula (V) in an inert organic solvent such as an ether, e.g. tetrahydrofuran, at the same temperature.

The sulphoxides of formula (VI) or (VII) or mixtures thereof may be obtained by the stereoselective oxidation of a product of formula:

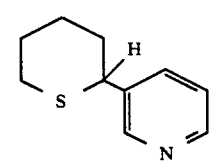

(VIII)

which generally takes the form of an R,S racemic mixture.

Oxidation of a product of the formula (VIII) by non-stereoselective conventional methods leads to a mixture of the sulphoxides of formulae (VI) and (VII) and the sulphoxides of formulae:

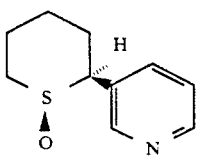

(IX)

and

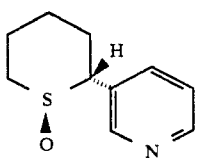

(X)

Only the sulphoxides of formulae (VI) and (VII) may be used for obtaining the active enantiomers which have the 1R,2R configuration.

The selective oxidation of a product of general formula (VIII) may be carried out either chemically or biochemically.

In general, the selective chemical oxidation is carried out in the presence of an asymmetry-inducing agent such as (+)-diethyl tartrate) and a titanium(IV) derivative such as a titanium alcoholate, for example titanium-(IV) isopropylate, by means of a hydroperoxide such as cumyl or tert-butyl hydroperoxide. In general, the reaction is performed in an organic solvent such as a halogenated aliphatic hydrocarbon, e.g. methylene chloride or 1,2-dichloroethane. The oxidation is preferably performed at a temperature in the region of −20° C.

The products of formulae (VI) and (VII) thereby obtained may be separated and purified by chromatography on a suitable support.

In general, the selective biochemical oxidation is carried out by means of a culture of a filamentous fungus or a filamentous bacterium, or by means of an enzyme isolated in the presence of an oxidizing agent [H. L. Holland, Chemical Reviews, 88, 473–485 (1988)]. Preferably, Aspergillus foetidus NRRL 337 is used. The oxidation is performed by adding a sterile solution of the product of formula (VIII), either to a culture of the microorganism in a suitable medium which has reached a sufficient degree of growth, and then continuing the incubation until a suitable degree of conversion of the product of formula (VIII) has been obtained, or to a solution of the enzyme containing an oxidizing agent such as hydrogen peroxide or tert-butyl hydroperoxide.

The products of formulae (VI) and (VII) are separated from the culture medium under the usual conditions, and are purified by chromatography on suitable supports.

The present invention also relates to the sulphoxides of formulae (VI) and (VII).

The product of formula (VIII) may be obtained according to one of the following methods, i.e.:

either by decarboxylation of the acid of formula:

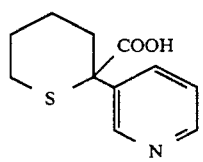

(XI)

by heating to a temperature of between 130° and 160° C., the acid of formula (XI) being obtained under the conditions described in European Patent EP 0,073,704.

or by the cyclization of a product of general formula:

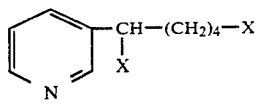

(XII)

optionally in salt form, in which X represents a halogen (chlorine, bromine) atom or a reactive ester residue (methylsulphonyloxy), by means of sodium sulphide, working in a two-phase aqueous-organic medium in the presence of a phase transfer catalyst such as a tetralkylammonium halide, e.g. tetrabutylammonium bromide.

The product of general formula (XII) may be obtained by the action of a halogenating agent (thionyl chloride) or an esterifying agent (methanesulphonyl chloride) on the diol of formula:

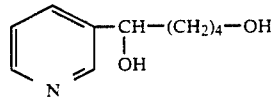

(XIII)

In general, when a halogenating agent is used, the reaction is performed in an organic solvent selected from halogenated aliphatic hydrocarbons such as methylene chloride or chloroform at a temperature of between 0° and 50° C., and when an esterifying agent is used, the reaction is performed in the presence of a basic agent (pyridine, triethylamine) at a temperature in the region of 0° C.

The product of formula (XIII) may be obtained by reduction of the keto alcohol of formula:

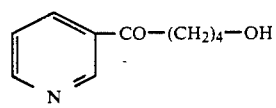

(XIV)

In general, the reduction is performed by means of an alkali metal borohydride such as sodium borohydride, working in an aqueous-alcoholic medium at a temperature in the region of 0° C.

The keto alcohol of formula (XIV) may be obtained by the action of 3-lithiopyridine on δ-valerolactone, it being possible for 3-lithiopyridine to be obtained by the action of a metalating agent such as butyllithium on a 3-halopyridine such as 3-bromopyridine.

In general, the reaction is performed in an inert organic solvent such as an ether (ethyl ether, tetrahydrofuran), optionally in the presence of an aliphatic hydrocarbon (hexane), at a temperature below −50° C. —Or by reduction of the (1RS,2RS) and/or (1RS,2SR) forms derived from the sulphoxide of formula:

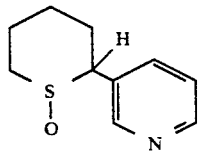

(XV)

by means of a sulphoxide-reducing agent such as an alkali metal hydrogen sulphite, e.g. sodium hydrogen sulphite, in aqueous solution.

The (1RS,2RS) and (1RS,2SR) forms derived from the sulphoxide of formula (XV) may be obtained by the cyclization of a product of formula:

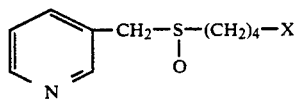

(XVI)

in which X is defined as above, by means of a base such as an alkali metal alcoholate (potassium tert-butylate), working in an inert organic solvent such as an ether, e.g. tetrahydrofuran.

The (1RS,2RS) and (1RS,2SR) forms derived from the product of formula (XV) may be separated by chromatography on suitable supports.

The product of formula (XVI) may be prepared under the conditions described in European Patent EP 0,097,584.

EXAMPLES

The following examples, given without implied limitation, show how the invention may be put into practice.

EXAMPLE 1

Sodium (0.24 g) is added to a solution, maintained at −40° C. under a nitrogen atmosphere, of ferric nitrate (0.05 g) in liquid ammonia (4 cc). The solution is stirred for 15 minutes at the same temperature, and this is followed by the successive addition of a solution of (−)-(1R,2R)-2-(3-pyridyl)-tetrahydrothiopyran 1-oxide ($[\alpha]_D^{20} = -219° \pm 2$; c=1, chloroform) (1 g) in anhydrous tetrahydrofuran (10 cc) in the course of 1 minute and then a solution of methyl isothiocyanate (0.5 g) in anhydrous tetrahydrofuran (2 cc) in the course of a few seconds. The mixture is stirred for 10 minutes at a temperature of between −40° C. and −35° C., ammonium chloride (0.6 g) is added, the temperature is allowed to rise gradually to about 20° C. and the mixture is then concentrated to dryness under reduced pressure (25 mm Hg; 3.4 kPa) at 30° C.

The mixture obtained, treated with saturated aqueous sodium chloride solution (10 cc), is extracted 3 times with methylene chloride (45 cc in total) and the combined organic extracts are dried over anhydrous magnesium sulphate, filtered and concentrated to dryness under reduced pressure (25 mm Hg; 3.4 kPa) at 30° C.

The product obtained (1.1 g) is dissolved in boiling ethyl acetate (130 cc). The solution is filtered while hot, cooled and then kept for 2 hours at a temperature in the region of 5° C. The crystals which have appeared are separated by filtration and dried under reduced pressure (2 mm Hg; 0.27 kPa) at 40° C.

(−)-(1R,2R)-N-Methyl-2-(3-pyridyl)tetrahydrothiopyran-2-carbothioamide 1-oxide (0.45 g), m.p. 244° C., is thereby obtained, its optical rotation being: $[\alpha]_D^{20} = -207.7° \pm 1.9$; c=1, chloroform.

EXAMPLE 2

Preparation of 2-(3-pyridyl)tetrahydrothiopyran 1-oxide-Chemical oxidation

Titanium(IV) isopropylate (12.4 g) and then distilled water (0.8 g) are added with stirring at a temperature in the region of 20° C. to a solution, maintained under a nitrogen atmosphere, of (+)-(diethyl tartrate) (18 g) in ethanol-free anhydrous methylene chloride (400 cc). The mixture is stirred for 25 minutes and cooled to −20° C., (RS)-2-(3-pyridyl)tetrahydrothiopyran (7.8 g) is added and 82% pure cumyl hydroperoxide (8.5 g) is then added dropwise in the course of 15 minutes. The mixture is stirred for 20 hours at −20° C. and then, after the addition of distilled water (20 cc), for 1 hours while allowing the temperature to rise gradually to 20° C. The mixture is filtered and the insoluble matter is washed 3 times with methylene chloride (450 cc in total). The combined filtrate and washings are washed with N sodium hydroxide (100 cc) and with saturated aqueous sodium chloride solution (200 cc), dried over anhydrous sodium sulphate, filtered and concentrated to dryness under reduced pressure (30 mm Hg; 4.1 kPa) at 40° C.

The product obtained (18 g) is chromatographed on neutral silica gel (0.063–0.200 mm) (180 g) contained in a column 4 cm in diameter. The column is eluted with a mixture of ethyl acetate and methanol (97:3 by volume), collecting 120-cc fractions. Fractions 17 to 29 are combined and concentrated to dryness under reduced pressure (30 mm Hg; 4.1 kPa) at 30° C.

The product obtained (1.5 g) is dissolved in boiling ethyl acetate (4.5 cc) and, after cooling, the solution is kept for 2 hours at a temperature in the region of 5° C. The crystals which have appeared are separated by filtration, washed with ethyl acetate (1 cc) and dried under reduced pressure (2 mm Hg; 2.6 kPa) at 45° C. A product (1.3 g) is obtained, a portion (1.1 g) of which is dissolved in boiling ethyl acetate (5.5 cc). After cooling, the solution is kept for 2 hours at a temperature in the region of 5° C. The crystals which have appeared are separated by filtration and dried under reduced pressure (2 mm Hg; 0.27 kPa) at 45° C.

(1R,2R)-2-(3-Pyridyl)tetrahydrothiopyran 1-oxide (1.1 g), m.p. 129° C., is thereby obtained, its optical rotation being:

$[\alpha]_D^{20} = -219° \pm 2$; c=1, chloroform.

Fractions 46 to 60 are combined and concentrated to dryness under reduced pressure (30 mm Hg; 4.1 kPa) at 30° C.

A mixture (3.0 g) of the (1R,2S) and (1S,2R) enantiomers of 2-(3-pyridyl)tetrahydrothiopyran 1-oxide, m.p. 109° C., is thereby obtained, its optical rotation being: $[\alpha]_D^{20} = -144° \pm 1.6$; c=1, chloroform.

(RS)-2-(3-Pyridyl)tetrahydrothiopyran may be prepared according to one of the following methods:

1) 2-(3-Pyridyl)tetrahydrothiopyran-2-carboxylic acid (32 g) is heated for 45 minutes to a temperature in the region of 140° C. After cooling, the product is chromatographed on neutral silica gel (0.060–0.200 mm) (200 g) contained in a column 4 cm in diameter. The column is eluted with methylene chloride, collecting 250-cc fractions. Fractions 4 to 14 are combined and concentrated to dryness under reduced pressure (25 mm Hg; 3.4 kPa) at 40°

C. (RS)-2-(3-Pyridyl)tetrahydrothiopyran (12.5 g), m.p. 49° C., is thereby obtained.

2-(3-Pyridyl)tetrahydrothiopyran-3-carboxylic acid may be prepared according to the method described in European Patent EP 0,073,704.

2) Toluene (20 cc), tetrabutylammonium bromide (0.06 g), sodium sulphide nonahydrate (3.6 g) and then 1,5-dichloro-5-(3-pyridyl)pentane hydrochloride (2.5 g) are added successively with stirring at 20° C. to a solution of sodium hydroxide (1.25 g) in water (1.25 g). The mixture is stirred for 1 hour 30 minutes at 70° C. and, after cooling, distilled water (10 cc) is then added. After settling has taken place, the aqueous phase is extracted 4 times with ether (80 cc in total). The organic extracts are combined, washed twice with distilled water (50 cc in total), dried over anhydrous sodium sulphate and concentrated to dryness under reduced pressure (25 mm Hg; 3.4 kPa) at 30° C.

The product thereby obtained (1.5 g) is chromatographed on neutral silica gel (0.063-0.200 mm) (7.5 g) contained in a column 1.5 cm in diameter. The column is eluted with ethyl acetate, collecting 100-cc fractions. Fraction 1 is concentrated to dryness under reduced pressure (25 mm Hg; 3.4 kPa) at 50° C.

(RS)-2-(3-Pyridyl)tetrahydrothiopyran (1.1 g), m.p. 49° C., is thereby obtained.

1,5-Dichloro-5-(3-pyridyl)pentane hydrochloride may be prepared in the following manner:

Thionyl chloride (21.4 g) is added dropwise in the course of 10 minutes at a temperature between 28° C. and 48° C. to a solution of 5-(3-pyridyl)-1,5-pentanediol (10.9 g) in chloroform (90 cc). The mixture is then kept boiling for 2 hours until gaseous evolution has ceased, cooled to 20° C. and kept at this temperature for 16 hours. After concentration to dryness under reduced pressure (25 mm Hg; 3.4 kPa) at 35° C., a residue (weighing 14.5 g) is obtained.

The product (14.5 g) obtained under the conditions described above is dissolved in a boiling mixture of isopropyl ether (50 cc) and isopropanol (75 cc). The solution, treated with decolorizing charcoal, is filtered while hot and the filtrate is washed 3 times with boiling isopropanol (300 cc in total). After the addition of isopropyl ether (700 cc), the mixture is cooled and kept for 2 hours at a temperature in the region of 5° C. The crystals which have appeared are separated by filtration, washed 3 times with isopropyl ether (300 cc in total) and dried under reduced pressure (25 mm Hg; 3.4 kPa) at 20° C.

1,5-Dichloro-5-(3-pyridyl)pentane hydrochloride (13.9 g) m.p. 123° C., is thereby obtained.

5-(3-Pyridyl)-1,5-pentanediol may be prepared in the following manner:

A solution of sodium borohydride (26.5 g) in a mixture (270 cc) of water and methanol (50:50 by volume) is added dropwise in the course of 20 minutes to a solution, maintained at a temperature in the region of 0° C., of 5-oxo-5-(3-pyridyl)-1-pentanol (25.7 g) in methanol (270 cc). The mixture is then stirred for 22 hours at a temperature in the region of 20° C. and thereafter concentrated to dryness under reduced pressure (25 mm Hg; 3.4 kPa) at 40° C.

The product obtained is dissolved in distilled water (200 cc) and the solution is saturated with sodium chloride. The oil which appears as an upper layer after settling has taken place is separated and dissolved in methanol (50 cc), dried over anhydrous sodium sulphate, filtered and concentrated to dryness under reduced pressure (25 mm Hg; 3.4 kPa) at 50° C. A first batch (18.2 g) is thereby obtained. The lower aqueous phase is extracted 3 times with chloroform (750 cc in total) and the organic extracts are combined, dried over anhydrous sodium sulphate, filtered and concentrated to dryness under reduced pressure (25 mm Hg; 3.4 kPa) at 50° C. A second batch (5.6 g) is thereby obtained.

The mixture of these two batches is chromatographed on silica gel (0.063-0.200 mm) (360 g) contained in a column 4.7 cm in diameter. The column is eluted with ethyl acetate, collecting 80-cc fractions. Fractions 44 to 72 are combined and concentrated to dryness under reduced pressure (25 mm Hg; 3.4 kPa) at 50° C. 5-(3-Pyridyl)-1,5-pentanediol (16.8 g) is thereby obtained in the form of a yellow oil [Rf=0.4; thin-layer chromatography on silica gel; solvent: ethyl acetate/methanol (80:20 by volume)].

5-Oxo-5-(3-pyridyl)-1-pentanol may be prepared in the following manner:

A solution of 3-bromopyridine (17.7 g) in anhydrous ether (100 cc) is added dropwise in the course of 20 minutes to a 1.6M solution (70 cc), maintained under a nitrogen atmosphere at a temperature in the region of −70° C., of n-butyllithium in hexane. After 30 minutes' stirring at the same temperature, a solution of δ-valerolactone (11.2 g) in anhydrous ether (200 cc) is added dropwise in the course of 20 minutes. The mixture is then stirred for 1 hour at a temperature in the region of −70° C., and thereafter for 2 hours 15 minutes while allowing the temperature to rise gradually to 16° C. Distilled water (150 cc) is added dropwise at a temperature in the region of 20° C. After settling has taken place, the aqueous phase is extracted 3 times with ethyl acetate (750 cc in total). The combined organic phases are washed twice with distilled water (500 cc in total), dried over anhydrous sodium sulphate, filtered and concentrated to dryness under reduced pressure (25 mm Hg; 3.4 kPa) at 45° C.

The product thereby obtained (18.1 g) is chromatographed on neutral silica gel (0.063-0.200 mm) (250 g) contained in a column 4.7 cm in diameter. The column is eluted with a cyclohexane/ethyl acetate mixture (50:50 by volume), collecting 90-cc fractions. Fractions 44 to 58 are combined and concentrated to dryness under reduced pressure (22 mm Hg; 3 kPa) at 40° C.

5-Oxo-5-(3-pyridyl)-1-pentanol (13.3 g) is thereby obtained in the form of a yellow oil (Rf=0.18; thin-layer chromatography on silica gel; solvent: ethyl acetate).

3) (1RS,2RS)-2-(3-Pyridyl)tetrahydrothiopyran 1-oxide (3.9 g) is dissolved in a 37.5% strength aqueous solution (25 cc) of sodium hydrogen sulphite. After heating to the boil for 22 hours and cooling, the solution is extracted 4 times with methylene chloride (100 cc in total) and the combined organic extracts are dried over anhydrous sodium sulphate, filtered and concentrated to dryness under reduced pressure (25 mm Hg; 3.4 kPa) at 35° C.

The product obtained (2.9 g) is chromatographed on neutral silica gel (0.040-0.063 mm) (325 g) contained in a column 5.5 cm in diameter. The column is eluted under reduced pressure (200 mm Hg; 25 kPa) with a mixture of cyclohexane and ethyl acetate (65:35 by volume), collecting 100-cc fractions. Fractions 11 to 27 are combined and concentrated to dryness under reduced pressure (25 mm Hg; 3.4 kPa) at 35° C.

(RS)-2-(3-Pyridyl)tetrahydrothiopyran (2.7 g), m.p. 49° C., is thereby obtained.

(1RS,2RS)-2-(3-Pyridyl)tetrahydrothiopyran 1-oxide may be prepared in the following manner:

A solution of 3-[(4-chlorobutyl)sulphinylmethyl]pyridine in anhydrous tetrahydrofuran (180 cc) is added dropwise in the course of 2 hours to a solution, maintained under a nitrogen atmosphere at a temperature in the region of 0° C., of potassium t-butylate (70.2 g) in anhydrous tetrahydrofuran (380 cc). The mixture is then stirred for 1 hour at the same temperature and thereafter for 16 hours at a temperature in the region of 20° C., treated with acetic acid (20 cc) and then filtered. The insoluble matter is washed 4 times with methylene chloride (580 cc in total) and the combined filtrates are concentrated to dryness under reduced pressure (20 mm Hg; 2.7 kPa) at 40° C.

The product obtained (61 g), with the addition of 82 g prepared under the same conditions, is chromatographed on neutral silica gel (0.063–0.200 mm) (600 g) contained in a column 6 cm in diameter. The column is eluted with a mixture (14.4 liters) of ethyl acetate and methanol (90:10 by volume) and then with a mixture (3.9 liters) of ethyl acetate and methanol (80:20 by volume), collecting 300-cc fractions. Fractions 21 to 35 are combined and concentrated to dryness under reduced pressure (20 mm Hg; 2.7 kPa) at 45° C.

The product obtained (25 g) is dissolved in boiling ethyl acetate (125 cc) and the solution, treated with decolorizing charcoal, is filtered while hot. After cooling, the solution is kept for 15 hours at a temperature in the region of 5° C. The crystals which have appeared are separated by filtration, washed three times with ethyl acetate (45 cc in total) and dried under reduced pressure (0.2 mm Hg; 0.027 kPa) at 50° C.

(1RS,2RS)-2-(3-Pyridyl)tetrahydrothiopyran 1-oxide (21.2 g), m.p. 130° C., is thereby obtained.

Fractions 49 to 52 are combined and concentrated to dryness under reduced pressure (20 mm Hg; 2.7 kPa) at 45° C. A first batch (10.4 g) is thereby obtained.

Fractions 53 to 61 are combined and concentrated to dryness under reduced pressure (20 mm Hg; 2.7 kPa) at 45° C. A second batch (9.9 g) is thereby obtained.

These first and second batches are recrystallized as described above in boiling ethyl acetate (90 cc and 100 cc, respectively) to give two new batches (7.3 g and 5.6 g).

The latter batches are combined and dissolved in boiling ethyl acetate (155 cc) and the solution, treated with decolorizing charcoal, is filtered while hot, cooled and kept for 16 hours at a temperature in the region of 5° C. The crystals which have appeared are separated by filtration, washed 3 times with ethyl acetate (30 cc in total) and dried under reduced pressure (0.2 mm Hg; 0.03 kPa) at 50° C.

(1RS,2SR)-2-(3-Pyridyl)tetrahydrothiopyran 1-oxide (10.4 g), m.p. 120° C., is thereby obtained.

EXAMPLE 3

Preparation of 2-(3-pyridyl)tetrahydrothiopyran 1-oxide-Biochemical oxidation

A culture medium having the following composition is prepared:

| | |
|---|---|
| glucose | 30 g |
| dipotassium phosphate | 4 g |
| sodium nitrate | 2 g |

-continued

| | |
|---|---|
| potassium chloride | 0.5 g |
| magnesium sulphate | 0.5 g |
| iron sulphate | 0.01 g |
| demineralized water q.s. | 1.000 cc |

The pH is adjusted to 4.3 by adding hydrochloric acid and the medium is sterilized in an autoclave for 30 minutes at 121° C., the glucose being sterilized separately.

Sterile culture medium (50 cc) contained in a 250-cc Erlenmeyer is inoculated with a suspension (2 cc) of Aspergillus foetidus NRRL 337 spores originating from an agar slant culture. The medium is incubated for 3 days at 28° C. on a table rotating at 200 rpm. An inoculum culture is thereby obtained, which is used to inoculate 10 identical Erlenmeyers each containing the culture medium (50 cc) described above. Each Erlenmeyer is inoculated with the inoculum culture (2 cc). The cultures are incubated for 4 days at 28° C. on a table rotating at 200 rpm.

A solution (2 cc), sterilized by filtration through a membrane, of (RS)-2-(3-pyridyl)tetrahydrothiopyran (10 mg) in water (2 cc) containing acetic acid (4%) is added to each of the 10 Erlenmeyers.

Culturing is continued for 5 days under the same conditions.

Analysis by thin-layer chromatography shows that the degree of conversion of the 2-(3-pyridyl)tetrahydrothiopyran is in the region of 60%.

Methanol (150 cc) is added to each of the 10 Erlenmeyers and the cultures are stirred for 30 minutes. After filtration and evaporation of the methanol under reduced pressure, the residual aqueous solution is percolated through a column containing octadecyl ($C_{18}$)-grafted silica (20 g). The column is washed with demineralized water to remove inorganic salts and the sulphoxides are then eluted with methanol (60 cc). The methanol eluate is concentrated to a volume of 5 cc and is then transferred to a column (height: 180 cm; diameter: 2.5 cm) containing Sephadex LH 20 (Pharmacia brand name) set up in pure methanol. The column is eluted at a constant flow rate of 0.7 cc/minute, collecting 5-cc fractions.

Fractions 48 to 55 contain unconverted (RS)-2-(3-pyridyl)tetrahydrothiopyran and, after evaporation of the solvent, fractions 61 to 74 yield a product (80 mg) consisting, according to analysis by high performance liquid chromatography on a chiral column, of a mixture of the (1R,2S) and (1R,2R) sulphoxides.

The (1R,2S) and (1R,2R) sulphoxides may be separated by a further chromatographic run on a Sephadex LH 20 column, performing the elution at a flow rate of 0.25 cc/minute and collecting 5-cc fractions.

Fractions 127 to 131 contain the (1R,2S) form, the optical rotation of which, determined in ethanol, is:

$$[\alpha]_D^{20} = -198° \pm 8°.$$

Fractions 138 to 142 contain the (1R,2R) form, the optical rotation of which, determined in ethanol, is:

$$[\alpha]_D^{20} = -202° \pm 5°.$$

The present invention also relates to medicinal products consisting of at least one product of general formula (IV), in the pure state or in the form of a composition in which it is combined with any other pharmaceutically compatible product, which can be inert or physiologically active. The medicinal products according to the invention may be used orally, parenterally or rectally.

As solid compositions for oral administration, tablets, pills, powders (in particular in hard gelatin capsules or wafer capsules) or granules may be used. In these compositions, the active product according to the invention is mixed with one or more inert diluents such as starch, cellulose, sucrose, lactose or silica. These compositions can also comprise substances other than diluents, e.g. one or more lubricants such as magnesium stearate, talc, colouring, a coating (dragees) or a varnish.

As liquid compositions for oral administration, pharmaceutically acceptable solutions, suspensions, emulsions, syrups and elixirs, containing inert diluents such as water, ethanol, glycerol, vegetable oils or liquid paraffin, may be used. These compositions can also comprise substances other than diluents, e.g. wetting products, sweeteners, thickeners, flavorings or stabilizers.

The sterile compositions for parenteral administration can preferably be solutions, aqueous or nonaqueous, suspensions or emulsions. As a solvent or vehicle, water, propylene glycol, a polyethylene glycol, vegetable oils, especially olive oil, injectable organic esters, e.g. ethyl oleate, or other suitable organic solvents may be employed. These compositions can also contain adjuvants, especially wetting agents, tonicity regulators, emulsifiers, dispersants and stabilizers. The sterilization may be carried out in several ways, e.g. by aseptic filtration, by incorporating sterilizing agents in the composition, by irradiation or by heating. They may also be prepared in the form of sterile solid compositions which can be dissolved at the time of use in a sterile injectable medium.

The compositions for rectal administration are suppositories or rectal capsules which contain, apart from the active product, excipients such as cocoa butter, semi-synthetic glycerides or polyethylene glycols.

In human therapy, the products of the invention are especially useful in the treatment of hypertension. The dosages depend on the effect sought and the treatment period; they are generally between 5 and 1,000 mg per day, administered orally, for an adult, in one or more doses.

Generally speaking, the doctor will determine the dosage he considers most appropriate in accordance with the age and weight and all other factors specific to the subject to be treated.

The example which follows, given without implied limitation, illustrates a composition according to the invention.

EXAMPLE

Tablets containing a 25 mg dose of active product and having the following composition are prepared according to the usual procedure:

| | |
|---|---|
| (1R,2R)-N-methyl-2-(3-pyridyl)tetra- | 25 mg |
| hydrothiopyran-2-carbothioamide 1-oxide | |
| starch | 60 mg |
| colloidal silica | 50 mg |
| magnesium stearate | 2 mg |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. A process for preparing (1R,2R)-2-(3-pyridyl)tetrahydrothiopyran-2-carbothioamide 1-oxides of formula:

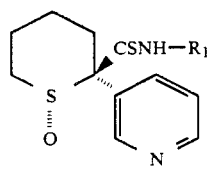

in which $R_1$ represents a linear or branched alkyl radical containing 1 to 4 carbon atoms, wherein an alkyl isothiocyanate of formula:

$$S=C=N-R_1$$

in which $R_1$ is defined as above, is reacted with previously anionized 1R,2R and 1R,2S sulphoxides of formulae:

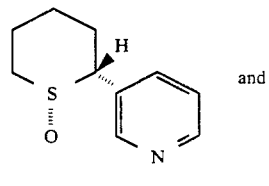

and

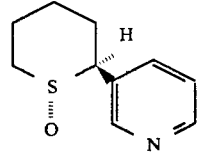

employed alone or mixed.

2. The process according to claim 1, wherein an alkyl isothiocyanate, dissolved in an inert organic solvent, is reacted with the sulphoxides employed alone or mixed, previously anionized by the action of sodium amide, in liquid ammonia at the boiling point of the reaction mixture, i.e. in the region of −30° C.

3. The process according to claim 1, wherein the sodium amide is prepared in situ.

* * * * *